US009902025B2

United States Patent
Shotton et al.

(10) Patent No.: US 9,902,025 B2
(45) Date of Patent: Feb. 27, 2018

(54) PROCESS FOR PRODUCING A SHAPE MEMORY SPIRAL ROTARY FILE

(71) Applicant: DENTSPLY International Inc., York, PA (US)

(72) Inventors: Vincent Shotton, Broken Arrow, OK (US); Dan Ammon, Tulsa, OK (US)

(73) Assignee: DENTSPLY International Inc., York, PA (US)

( * ) Notice: Subject to any disclaimer, the term of this patent is extended or adjusted under 35 U.S.C. 154(b) by 492 days.

(21) Appl. No.: 14/329,868

(22) Filed: Jul. 11, 2014

(65) Prior Publication Data

US 2015/0164615 A1    Jun. 18, 2015

Related U.S. Application Data

(60) Provisional application No. 61/844,980, filed on Jul. 11, 2013.

(51) Int. Cl.
| | |
|---|---|
| *B23P 15/44* | (2006.01) |
| *B21K 5/12* | (2006.01) |
| *A61C 5/42* | (2017.01) |
| *B21D 37/16* | (2006.01) |

(52) U.S. Cl.
CPC ............. *B23P 15/44* (2013.01); *A61C 5/42* (2017.02); *B21K 5/12* (2013.01); *B21D 37/16* (2013.01); *Y10T 29/49826* (2015.01)

(58) Field of Classification Search
CPC ....... A61C 5/42; Y10T 29/49567; B21D 7/16; B21D 7/00; B21D 37/08; B21D 43/05; B21D 37/16; B21C 3/06; B21C 25/08; B21C 25/02; B23P 15/28; B23P 15/44; B21K 5/12
USPC .............. 72/472, 470, 468, 467, 416, 414; 29/896.1, 896.11
See application file for complete search history.

(56) References Cited

U.S. PATENT DOCUMENTS

| | | | |
|---|---|---|---|
| 2007/0101797 A1* | 5/2007 | Quan ................. | A61O 5/42 72/416 |
| 2010/0233648 A1* | 9/2010 | McSpadden ........... | A61O 5/42 29/896.11 |
| 2011/0271529 A1 | 11/2011 | Gao et al. | |

FOREIGN PATENT DOCUMENTS

| | | |
|---|---|---|
| WO | 2010030668 A1 | 3/2010 |
| WO | 2010080586 A1 | 7/2010 |
| WO | 2011062970 A1 | 5/2011 |

OTHER PUBLICATIONS

PCT International Search Report.
PCT Written Opinion.

* cited by examiner

*Primary Examiner* — R. K. Arundale
*Assistant Examiner* — Pradeep C Battula
(74) *Attorney, Agent, or Firm* — David A. Zdurne; Douglas J. Hura; Leana Levin

(57) ABSTRACT

A method for manufacturing at least one nonlinear file including the steps of deforming at least a portion of a linear file away from a file axis and heat-treating the deformed file to shape-set the nonlinear file.

29 Claims, 10 Drawing Sheets

PROCESS FOR PRODUCING A SHAPE MEMORY SPIRAL ROTARY FILE

CROSS-REFERENCE TO RELATED APPLICATIONS

This patent application claims the benefit of and priority to U.S. Provisional Application Ser. No. 61/844,980, filed on Jul. 11, 2013, which is herein incorporated by reference for all purposes.

FIELD OF INVENTION

The present invention is directed to a method for treating a dental instrument, and specifically to a rotary file useful for shaping and cleaning root canals.

BACKGROUND OF THE INVENTION

The endodontic instruments (including files and reamers) are used for cleaning and shaping the root canals of infected teeth. They may be in mode of either rotation or reciprocation in the canal by dentists, either manually or with the aid of dental handpieces onto which the instruments are mounted. Instruments are generally used in sequence (depending on different root canal surgery techniques) in order to achieve the desired outcome of cleaning and shaping. The endodontic instrument is subjected to substantial cyclic bending and torsional stresses as it is used in the process of cleaning and shaping a root canal. Because of the complex curvature of root canals, a variety of unwanted procedural accidents such as ledging, transportation, perforation, or instrument separation, can be encountered in the practice of endodontics.

Currently, endodontic rotary instruments made of Shape Memory Alloys (SMA) have shown better overall performance than stainless steel counterparts. However, the occurrence of unwanted procedural accidents mentioned above has not been drastically reduced. Therefore, it necessitates new endodontic instruments with improved overall properties, especially flexibility and resistance to fracture either due to cyclic fatigue and torsional overload.

U.S. Pat. No. 4,889,487 discusses an endodontic file having one or more elongated, bow-shaped bends for being used to enlarge and shape the root canal. Since not all root canals have the same geometry, a conventional tapered file typically produces a circular cross-section thereby limiting the removing the dentin and soft tissue from the canal to generally one sized canal opening corresponding to the circular-cross-section of the conventional file. This patent discusses crimping the file between to stamping member to shape the file to the desired bend radius. The problem with crimping a file is that the tool used to crimp may potentially damage the fluting of the file thus making less efficient in cutting. Another issue with crimping a file is that it inherently weakens the file in that crimped area thus making it more susceptible to breaking within the canal. U.S. Pat. No. 7,713,059 discusses an instrument for cleaning and/or shaping and/or widening a channel for a root canal. This design having an inner volume enclosed by the instrument and its outer contour may be allowed to change as a result of the forces exerted on it while working.

One possibly advantage of the present invention as compared to conventional rotary files is a method for forming a nonlinear file. Another possibly advantage of the present invention as compared to conventional rotary files is a method for forming a nonlinear superelastic file that may be able to change shape and geometry by either expanding or collapsing while shaping a root canal. Also, by shaping the rotary file with this process of using a fixture to shape set a shape memory alloy (e.g., NiTi), it may prevent the fluting from being damaged as well as maintaining the geometry throughout the process of preparing a root canal.

The advantage to this type of rotary file design as compared to conventional rotary files is in its ability to change shape and geometry by either expanding or collapsing while shaping a root canal. Also, by shaping the rotary file with this process of using a fixture to shape set Nickel Titanium, it prevents the fluting from being damaged as well as maintaining the geometry throughout the process of instrumenting a root canal. U.S. Pat. No. 4,889,487 discusses a method of crimping a file to obtain the desired shape. The problem with crimping a file is that the tool used to crimp will potentially damage the fluting of the file thus making less efficient in cutting. Another issue with crimping a file is that it inherently weakens the file in that crimped area thus making it more susceptible to breaking within the canal. By shape setting the file in a fixture that does not damage the flutes, it allows the file to be stronger and more efficient in cutting as compared to the invention discussed in U.S. Pat. No. 4,889,487.

SUMMARY OF THE INVENTION

The present invention seeks to improve upon prior endodontic instruments by providing an improved process for manufacturing endodontic instruments. In one aspect, the present invention provides a method for manufacturing a nonlinear file (e.g., nonlinear superelastic file) comprising the steps of: providing a file having a shaft and a file axis; providing a first fixture having a first file groove for receiving the shaft, the first file groove being defined by one or more first displacement members; inserting at least one portion of the shaft into the first file groove, the at least one portion of the shaft including a first portion of the shaft; contacting the first portion of the shaft with a first displacement member of the one or more first displacement members such that the first portion of the shaft is displaced from the file axis thereby forming a first offset portion of the shaft, the first offset portion of the shaft and the file axis defining a first file plane; and heating the first offset portion of the shaft while inserted in the first fixture to a temperature from about 200° C. to less than the melting point of the file for a time period from about 1 minute to about 640 minutes to shape-set the first offset portion of the shaft thereby forming a shape-set nonlinear file.

In another aspect, the present invention contemplates a method for manufacturing a nonlinear file comprising the steps of: providing a linear file having a shaft and a file axis; providing a first fixture having a first mating portion and a second mating portion, each mating portion including a surface, at least one of the surfaces of the first and second mating portions having a first file groove for receiving the shaft, the first file groove extending along a first groove plane that is defined by a first groove axis and one or more first displacement members; inserting a first portion of the shaft into the first file groove so that the file axis along the first portion of the shaft and the first groove axis along the first file groove are generally coaxial; moving at least one of surfaces towards one another so that a first displacement member of the one or more first displacement members displaces the first portion of the shaft from the file axis along the first groove plane thereby forming a first offset portion of the shaft, the first offset portion of the shaft and the file axis defining a first file plane; heating the first offset portion of the shaft while inserted in the first fixture to a temperature from about 200° C. to less than the melting point of the file for a time period greater than 5 minutes but less than about 640 minutes to shape-set the first offset portion of the shaft thereby forming a shape-set nonlinear file; removing the shape-set nonlinear file from the first fixture; providing a second fixture having a first mating portion and a second mating portion, each mating portion including a surface, at least one of the surfaces of the first and second mating portions having a second file groove for receiving a nonlinear shaft of the shape-set nonlinear file, the second file groove having a second groove axis, one or more second displacement members, and a second groove opening that extends along the at least one of the surfaces of the first and second mating portions, the second groove opening generally corresponding to the shape of the first offset portion along the first file plane; inserting a first portion of the nonlinear shaft into the second groove opening; moving at least one of surfaces towards one another so that a first displacement member of the one or more second displacement members displaces the first portion of the nonlinear shaft away from the first file plane thereby forming a second offset portion of the nonlinear file; and heating the second offset portion of the shaft while inserted in the second fixture to a temperature from about 200° C. to less than the melting point of the file for a time period greater than 5 minutes but less than about 640 minutes to shape-set the second offset portion of the nonlinear file thereby forming a shape-set three-dimensional nonlinear file.

In another aspect, the present invention contemplates a method for manufacturing a nonlinear file comprising the steps of: providing a plurality of files having a shaft and a file axis; providing a first fixture having a first mating portion and a second mating portion, each mating portion including a surface with a plurality of first file grooves having a first groove opening for receiving at least a portion of the shafts of the plurality of files, the first file grooves of the first mating portion surface corresponding to the opposing first file groove of the second mating portion, wherein the groove openings include a base surface having one or more first displacement members; inserting a first portion of the shafts into the first file grooves along the groove openings, wherein the groove openings generally correspond to the shape of the first portion of the shafts along the file axes; moving at least one of surfaces towards one another so that a first displacement member of the one or more first displacement members displaces the first portion of the shafts from the file axes thereby forming a plurality first offset portions of the shafts, each first offset portion of each shaft and each file axis define a first file plane; heating the first offset portions of the shafts while inserted in the first fixture to a temperature from about 200° C. to less than the melting point of the file for a time period from about 5 minutes to about 640 minutes to shape-set the first offset portions of the shafts thereby forming a plurality of shape-set nonlinear files; removing the shape-set nonlinear files from the first fixture; providing a second fixture having a first mating portion and a second mating portion, each including a surface, the surfaces of the first and second mating portions having a plurality of second file grooves with second groove openings extending along the respective surface, the second file grooves of the first mating portion surface corresponding to the opposing first file grooves of the second mating portion, wherein the second groove openings include a base surface having one or more second displacement members; inserting a first portion of a nonlinear shafts of the nonlinear files into the second groove openings; moving at least one of surfaces towards one another so that a first displacement member of the one or more second displacement members of each of the second file grooves displaces the first portion of the nonlinear shafts away from the first file planes thereby forming a second offset portion of the nonlinear files; and heating the second offset portion of the nonlinear shafts while inserted in the second fixture to a temperature from about 200° C. to less than the melting point of the files for a time period from about 5 minutes to about 640 minutes to shape-set the second offset portion of the nonlinear shafts thereby forming a plurality of shape-set three-dimensional nonlinear files.

In yet another aspect, any of the aspects of the present invention may be further characterized by one or any combination of the following features: wherein the method further comprise the steps of: providing a second fixture having a second file groove for receiving the shaft of the shape-set nonlinear file, the second file groove being defined by one or more second displacement members; inserting the first portion, a second portion, or both of the shaft of the shape-set nonlinear file into the second file groove; contacting the first portion, the second portion, or both of the shaft with a first displacement member of the one or more second displacement members such that the first portion, the second portion, or both of the shaft is displaced from the first file plane thereby forming a second offset portion of the shaft, the second offset portion of the shaft and the file axis defines a second plane that is different from the first plane; and heating the second offset portion of the shaft while inserted in the second fixture to a temperature from about 200° C. to less than the melting point of the file for a time period from about 1 minute to about 640 minutes to shape-set the second offset portion of the shaft thereby forming a shape-set three-dimensional nonlinear file; wherein the shape-set nonlinear file is removed from the first fixture prior to being inserted into the second fixture; wherein the file is formed of a material selected from the group consisting of nickel, titanium, and mixtures thereof; wherein the shape-set nonlinear file is a shape-set nonlinear superelastic file; wherein the first offset portion of the shaft along the first file plane is orientated along the second groove plane of the second file groove, wherein the shape of the first offset portion of the shaft along the first file plane generally corresponds to the shape of the second file groove along the second groove plane; wherein the heating step, the portion of the shaft is heated to a temperature from about 300° C. to about 650° C. for a time period from about 1 minute to about 45 minute to shape-set the portion of the shaft thereby forming the shape-set nonlinear file; wherein the heating step, the portion of the shaft is heated to a temperature from about 350° C. to about 600° C. for a time period from about 3 minutes to about 30 minutes to shape-set the portion of the shaft thereby forming the shape-set nonlinear file; wherein the heating step, the portion of the shaft is heated to a temperature from about 450° C. to about 550° C. for a time period from about 5 minutes to about 20 minutes to shape-set the portion of the shaft thereby forming the shape-set nonlinear file; wherein the heating step, the portion of the shaft is heated to a temperature from about 300° C. to about 650° C. for a time period from about 1 minute to about 45 minute to shape-set the portion of the shaft thereby forming the shape-set nonlinear file; wherein the heating step, the portion of the shaft is heated to a temperature from about 350° C. to about 600° C. for a time period from about 3 minutes to about 30 minutes to shape-set the portion of the shaft thereby forming the shape-set nonlinear file; wherein the heating step, the portion of the shaft is heated to a temperature from about 450° C. to about 550° C. for a time period from about 5 minutes to about 20 minutes to shape-set the portion of the shaft thereby forming the shape-set nonlinear file; further comprising the step of contacting a second portion of the shaft with a second displacement member of the one or more displacement members such that the second portion of the shaft is displaced from the file axis thereby forming a second offset portion of the shaft, wherein the first offset portion of the shaft and the file axis define a first plane and the second offset portion defines a second plane different from the first plane; further comprising the step of contacting a second portion of the shaft with a second displacement member of the one or more displacement members such that the second portion of the shaft is displaced from the file axis thereby forming a second offset portion of the shaft, wherein the first offset portion of the shaft and the file axis define a first plane and the second offset portion defines a second plane different from the first plane; wherein the first offset portion of the shaft along the first file plane is orientated along the second groove plane of the second file groove, wherein the shape of the first offset portion of the shaft along the first file plane generally corresponds to the shape of the second file groove along the second groove plane; wherein the heating step, the first offset portion, the second offset portion, or both is heated to a temperature from about 300° C. to about 650° C. for a time period from about 5 minutes to about 45 minute to shape-set the portion of the shaft thereby forming the shape-set nonlinear file; wherein the heating step, the first offset portion, the second offset portion, or both is heated to a temperature from about 350° C. to about 600° C. for a time period from about 7 minutes to about 30 minutes to shape-set the portion of the shaft thereby forming the shape-set nonlinear file; wherein the heating step, the first offset portion, the second offset portion, or both is heated to a temperature from about 450° C. to about 550° C. for a time period from about 8 minutes to about 20 minutes to shape-set the portion of the shaft thereby forming the shape-set nonlinear file; further comprising the step of contacting a second portion of the shaft with a second displacement member of the one or more first displacement members such that the second portion of the shaft is displaced from the file axis thereby forming a third offset portion of the shaft, wherein the first offset portion and third offset portion of the shaft and the file axis define a first plane and the second offset portion defines a second plane different from the first plane; wherein the first offset portions of the shafts along the first file planes are orientated along the second groove planes of the second file grooves, wherein the shape of the first offset portions of the shafts along the first file planes generally correspond to the shape of the second file grooves along the second groove planes; wherein the heating step, the first offset portions, the second offset portions, or both are heated to a temperature from about 300° C. to about 650° C. for a time period from about 5 minutes to about 45 minute to shape-set the portions of the shafts thereby forming the shape-set nonlinear files; wherein the heating step, the first offset portions, the second offset portions, or both are heated to a temperature from about 350° C. to about 600° C. for a time period from about 7 minutes to about 30 minutes to shape-set the portions of the shafts thereby forming the shape-set nonlinear files; wherein the heating step, the first offset portions, the second offset portions, or both is heated to a temperature from about 450° C. to about 550° C. for a time period from about 8 minutes to about 20 minutes to shape-set the portions of the shafts thereby forming the shape-set nonlinear files; further comprising the step of contacting a second portion of the shafts with a second displacement member of the one or more first displacement members of each first file groove such that the second portions of the shafts are displaced from the file axes thereby forming a third offset portion of the shafts, wherein the first offset portions and third offset portions of the shafts and the file axes define a plurality of first planes and the second offset portions defines a plurality of second planes different from the first planes; or any combination thereof; further comprising the step of providing a handle and attaching the handle to a portion of the nonlinear hand file; or any combination thereof.

It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise.

DETAILED DESCRIPTION OF THE INVENTION

Figure 1:
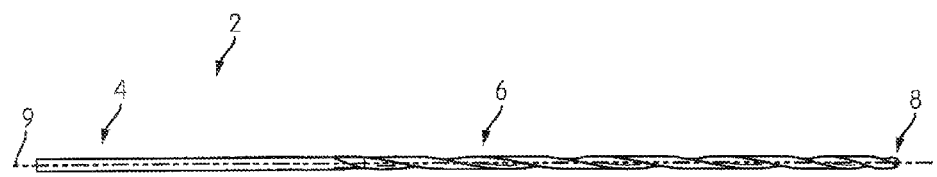
FIG. 1 is a perspective view of a non-shaped-set endodontic file.

Previous shape-setting method have been described in co-pending application U.S. Ser. No. 13/300,506, which is herein incorporated by reference for all purposes. It is appreciated that the method for forming the shape-setting file generally includes inserting a file into a fixture that includes deformation members for deforming at least one portion of the file. The file 2 may include a handle portion 4, a shaft portion 6 with a tip 8. As seen in FIG. 1. The starting shape of the file is generally linear and extends along a file axis 9. However, other starting shapes are contemplated such as a two-dimensional (2D) shape. The present invention utilizes at least one set fixture (for starting files having a 2D shape) and preferably at least two different shape set fixtures to bend and set the geometry of the file to the desired finished shape (e.g., a three-dimensional (3D) shape. It is appreciated that the fixture(s) is heated to a temperature of at least about 200° C., at least about 350° C., and preferably at least about 400° C. to accomplish the shape-setting of the file. Furthermore, it is appreciated that the fixtures are heated to a temperature less than about 650° C., less than about 625° C., and preferably less than about 600° C. to accomplish the shape-setting of the file. For example, the temperature of the fixtures may range from about 200° C. to about 650° C., from about 350° C. to about 625° C., and preferably from about 400° C. to about 600° C. to accomplish the shape-setting of the file. More specifically, it is appreciated that the files are heated in the fixtures for a period of time that is at least about 1 minute, at least about 3 minutes, and preferable at least about 5 minutes (though at least about 6 minutes, at least about 8 minutes is also contemplated) to accomplish the shape-setting. Furthermore, it is appreciated that the files are heated in the fixtures for a period of time that is less than about 640 minutes, less than about 320 minutes, less than about 60 minutes, less than about 30 minutes, and preferably less than about 15 minutes to accomplish the shape setting. For example, the period of time may range from about 1 minute to about 640 minutes, from about 3 minutes to about 320 minutes, from about 5 minutes to about 60 minutes, from about 5 minutes (e.g., 6 minutes) to about 30 minutes and preferably from about 5 minutes (e.g., about 8 minutes) to about 15 minutes to accomplish the shape-setting of the file.

Figure 2:
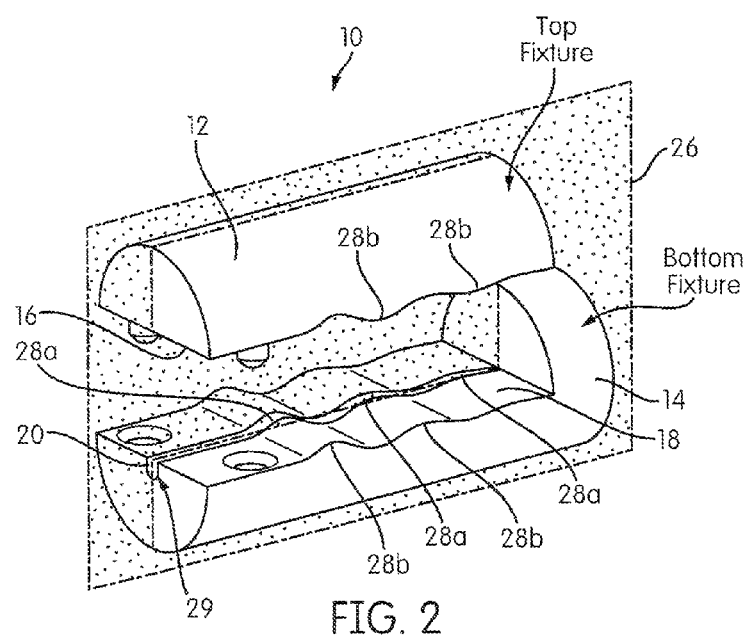
FIG. 2 is a perspective view of a first embodiment of the present invention in an open position.
Figure 3:
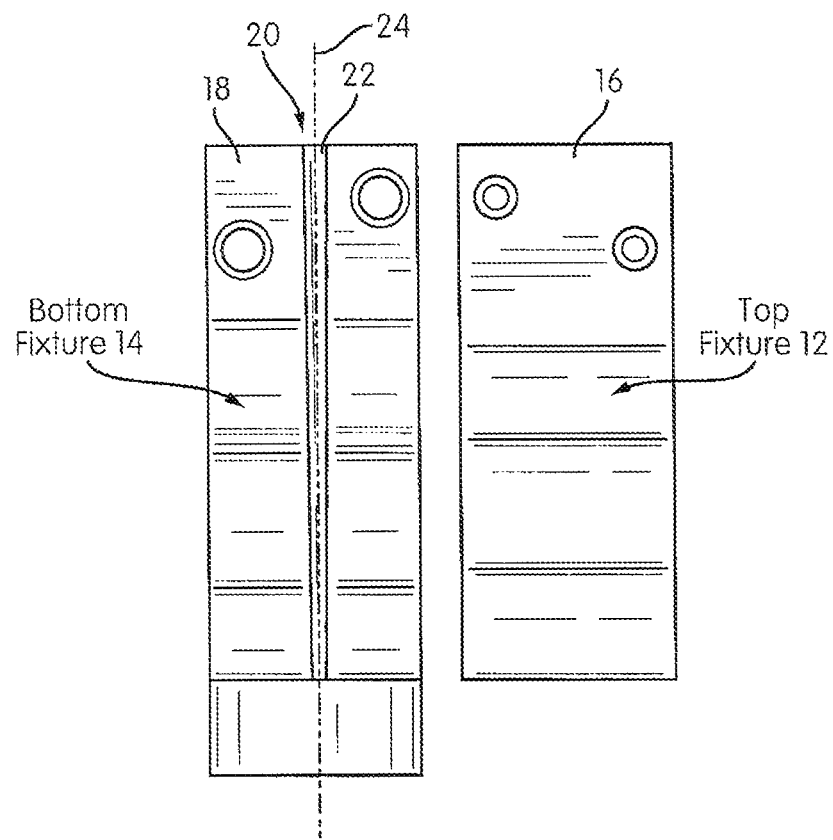
FIG. 3 is a top view of the first embodiment shown in FIG. 2.

In one specific embodiment, the first fixture 10 may be a two-dimensional (2D) fixture. This fixture includes a first mating portion 12 and a second mating portion 14. The first mating portion 12 having an outer surface 16 that generally opposes an outer surface 18 of the second mating portion 14 while in the closed position. At least one of the surfaces 16, 18 having a file groove 20 extending along the respective surface. The file groove 20 includes a groove opening 22 for receiving at least a portion and a groove axis 24 (FIG. 3). It is appreciated, that the first fixture 10 may be utilized to shape-set the linear file 2 in one plane (e.g., a first groove plane 26). The first groove 20, the surface of the first mating portion, the surface of the second mating surface 18, or combinations thereof may include one or more deformation members 28 for deforming the linear file 2 from the file axis 9. As shown in FIG. 2, a first groove 20 is provided along the surface of the second mating portion 18 and includes a plurality of deformation members 28a. Additionally, the surfaces 16, 18 of the first and second mating portions 12, 14 first groove 20 include a plurality of deformation members 28b, generally corresponding to the deformation members 28a of the first file groove 20. In a preferred embodiment, the first file groove 20 includes a base surface 29 that is at least partially defined by the deformation members 28a, the deformation members 28a being in the shape of curves that rise and descend towards and away, respectively, from the groove axis about the first groove plane.

Figure 5:
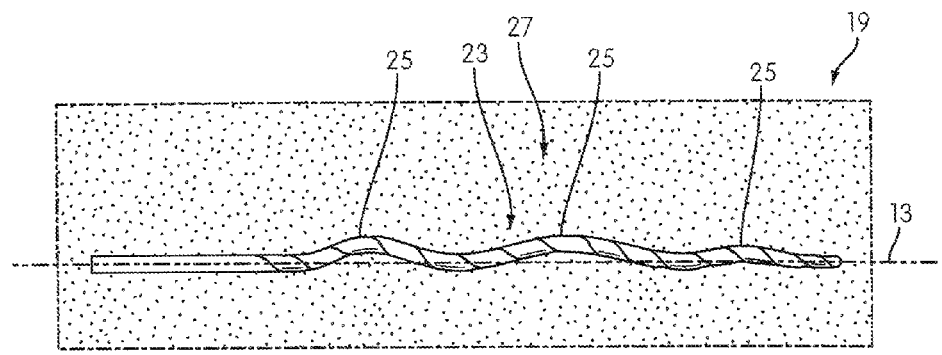
FIG. 5 is a cross-sectional side view of the first embodiment shown in FIG. 2 in a closed position with an endodontic file disposed therein.

The method for forming a 2D shape-set non-linear file may generally include inserting a linear file into the first file groove along the groove opening and moving the first and second mating portions to a closed position. As the surfaces approach one another, the deformation members contact portions of the shaft to deform the shaft away from the file axis 9 (e.g., along the groove plane 26) thereby forming an offset portion 25 of the shaft by forcing the portion of the shat into a 2D orientation. It is appreciated that the offset portion 25 relative to the file axis defines a first file plane 19. Thereafter, the first fixture is heat-treated thereby forming a shape-set nonlinear 2D file 27 (FIG. 5).

It is appreciated that the process of producing the 2D file (or 3D file) may be by placing the a shape memory alloy (SMA) such as Nickel-Titanium (NiTi) based systems, Cu based systems Fe based systems, or any combination thereof (e.g., materials selected from a group consisting of near-equiatomic Ni—Ti, Ni—Ti—Nb alloys, Ni—Ti—Fe alloys, Ni—Ti—Cu alloys, beta-phase titanium and combinations thereof) file into the 2D fixture and/or 3D fixture and where the fixture is maintained at a desired temperature where it shape sets the file to the desired geometry.

The present invention may further include a second fixture 30 that is a three-dimensional (3D) fixture. After the linear file has been shape set using the 2D first fixture 10, the file may be placed into the 3D fixture where the file is then shape set in 3 dimensions into a spiral shape, cork shape, off-centered shape, combinations thereof, or otherwise.

The second (set) fixture 30 includes a first mating portion 32 and a second mating portion 34. The first mating portion 32 having an outer surface 36 that generally opposes an outer surface 38 of the second mating portion 34 while in the closed position. In this second fixture 30, both surfaces 36,38 include a second file groove 40 which extend along the respective surface. The second file grooves 40 include a second groove opening 42 for receiving at least a portion (at least one offset portion 25) of the non-linear 2D shaft 23. The second groove openings 40 may be shaped to receive the non-linear shaft 23 in a mating relationship. Preferably, the shapes of the second groove openings 42 are also non-linear and dimensioned to receive the non-linear shaft 23 (or a portion thereof) as it is orientated in the first file plane. More specifically, the second groove openings 42 have an s-shaped configuration along a second groove plane 43 that corresponds to the s-shaped configuration of the non-linear shaft 23 about the first file plane 19, though not required.

Figure 6:
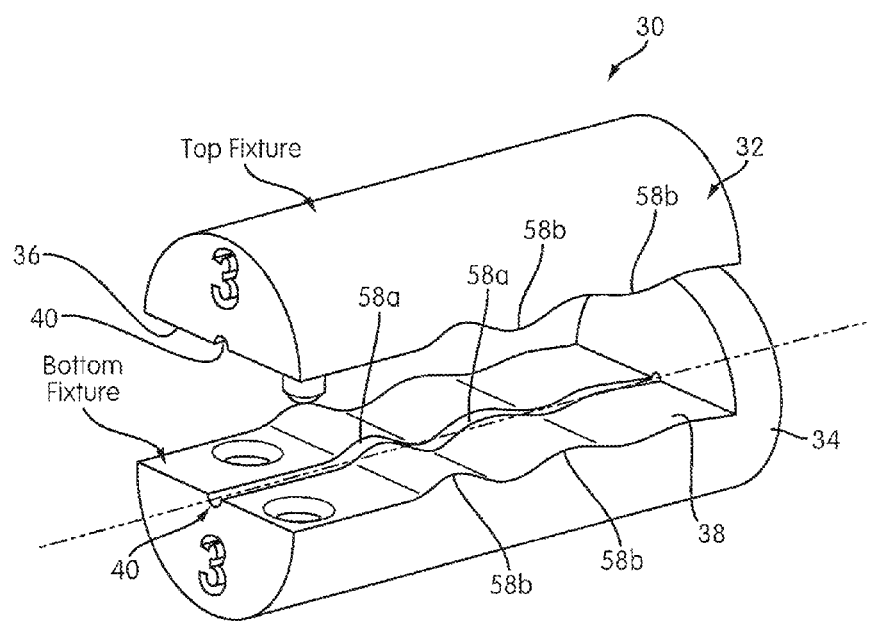
FIG. 6 is a perspective view of a second embodiment of the present invention in an open position.
Figure 9:
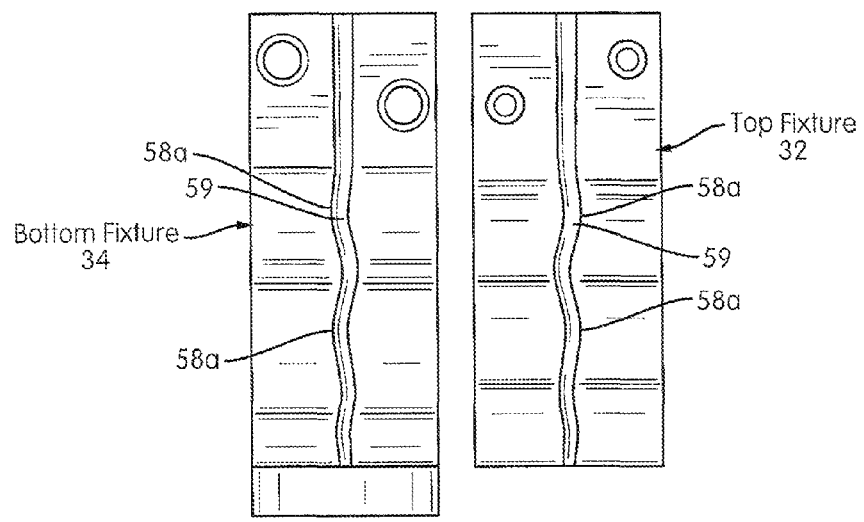
FIG. 9 is a top view of the internal surfaces of the two portions of the second embodiment shown in FIG. 6.
Figure 10:
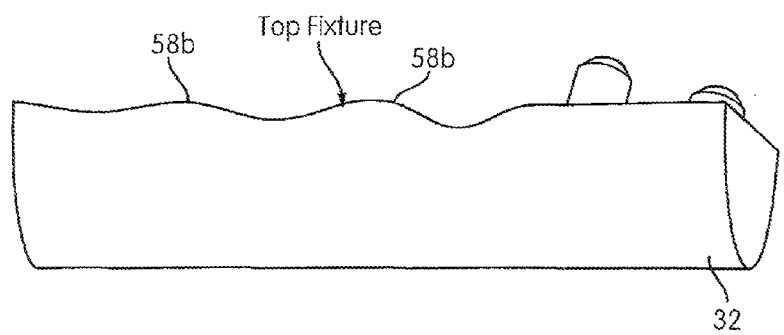
FIG. 10 is a side perspective view of a portion of the second embodiment shown in FIG. 6.

It is appreciated, that the second fixture 30 may be utilized to shape-set the non-linear shaft 23 in a second plane (e.g., a third groove plane 46). The second grooves 40, the surface 36 of the first mating portion 32, the surface 38 of the second mating portion 34, or combinations thereof may include one or more deformation members 48 for deforming the non-linear shaft 23 from the file axis 13. As shown in FIG. 6, a second groove 40 is provided along both surfaces 46,48 of the first and second mating portions 42,44 and includes a plurality of deformation members 58a (FIG. 9). Optionally, the surfaces 46,48 of the first and second mating portions 42,44 include a plurality of deformation members 58b, generally corresponding to the deformation members 58a of the second file grooves 40 to aid in aligning the first and second mating portions and maintaining them in the closed position. In a preferred embodiment, the second file grooves 40 includes a base surface 59 that is at least partially defined by the deformation members 58a, the deformation members 58a being in the shape of curves that rise and descend towards and away from the groove axis about the first groove plane, however, other shapes of the deformation members are contemplated.

Figure 7:
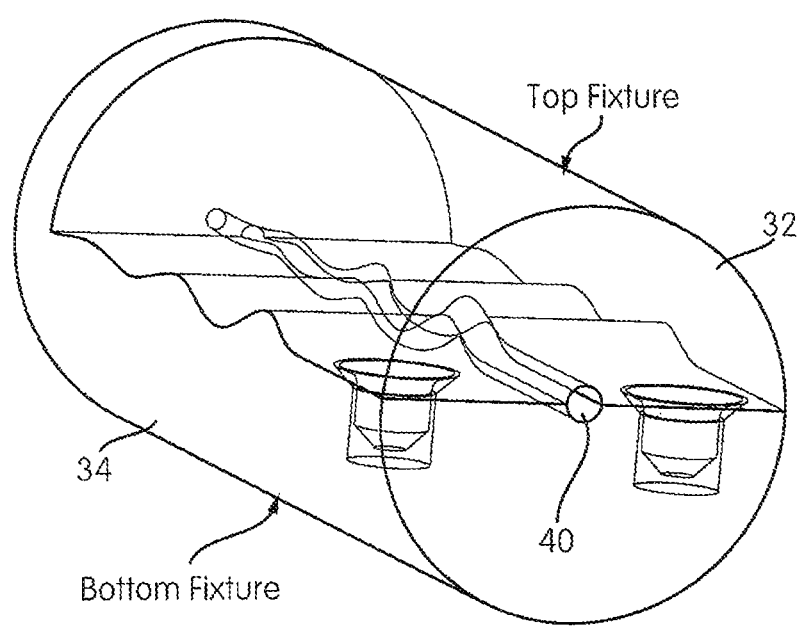
FIG. 7 is a transparent perspective view of the second embodiment shown in FIG. 6 in a closed position.
Figure 8:
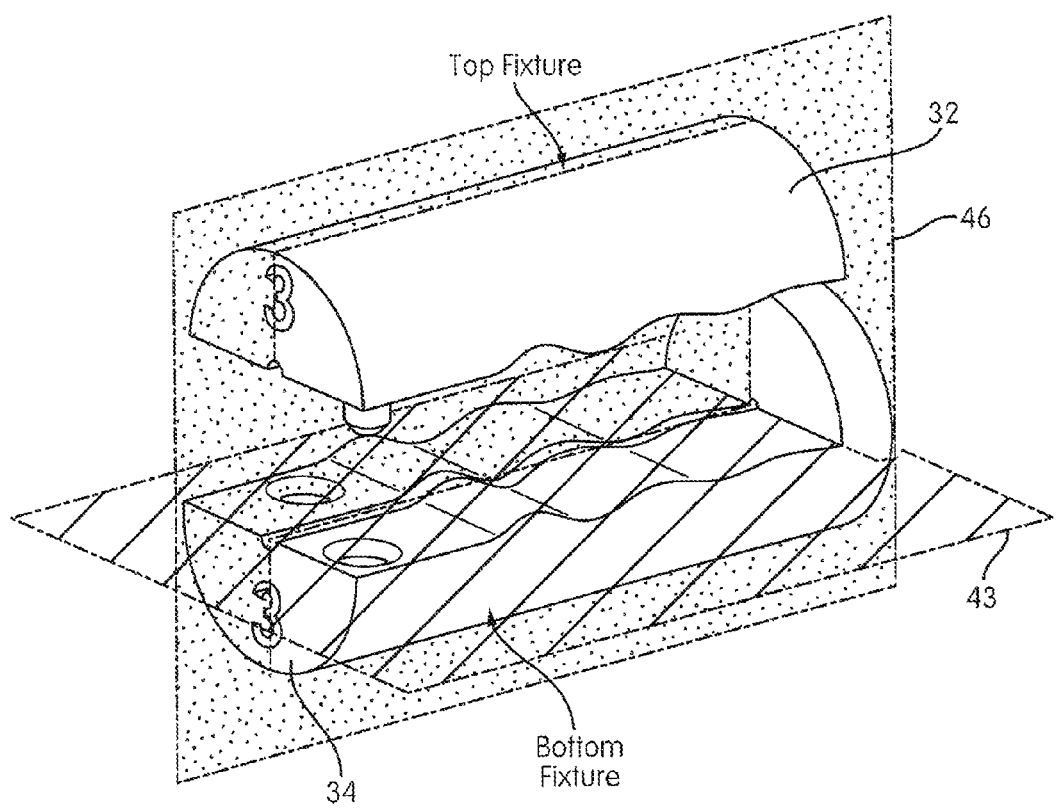
FIG. 8 is another perspective view of the second embodiment shown in FIG. 6.

FIG. 7 provides a transparent showing of the second fixture in the closed position without the nonlinear file inserted therein.

Figure 4:
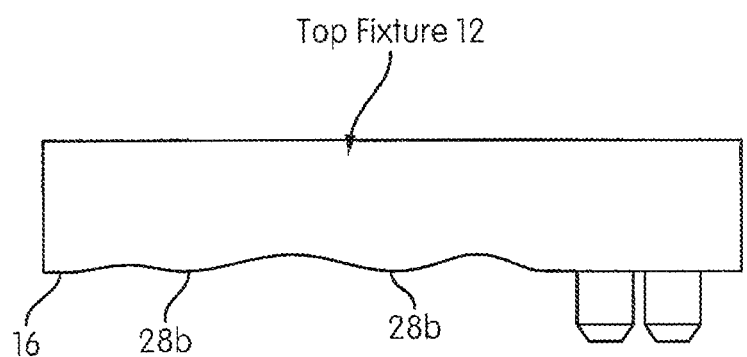
FIG. 4 is a side view of a portion of the first embodiment shown in FIG. 2.
Figure 11:
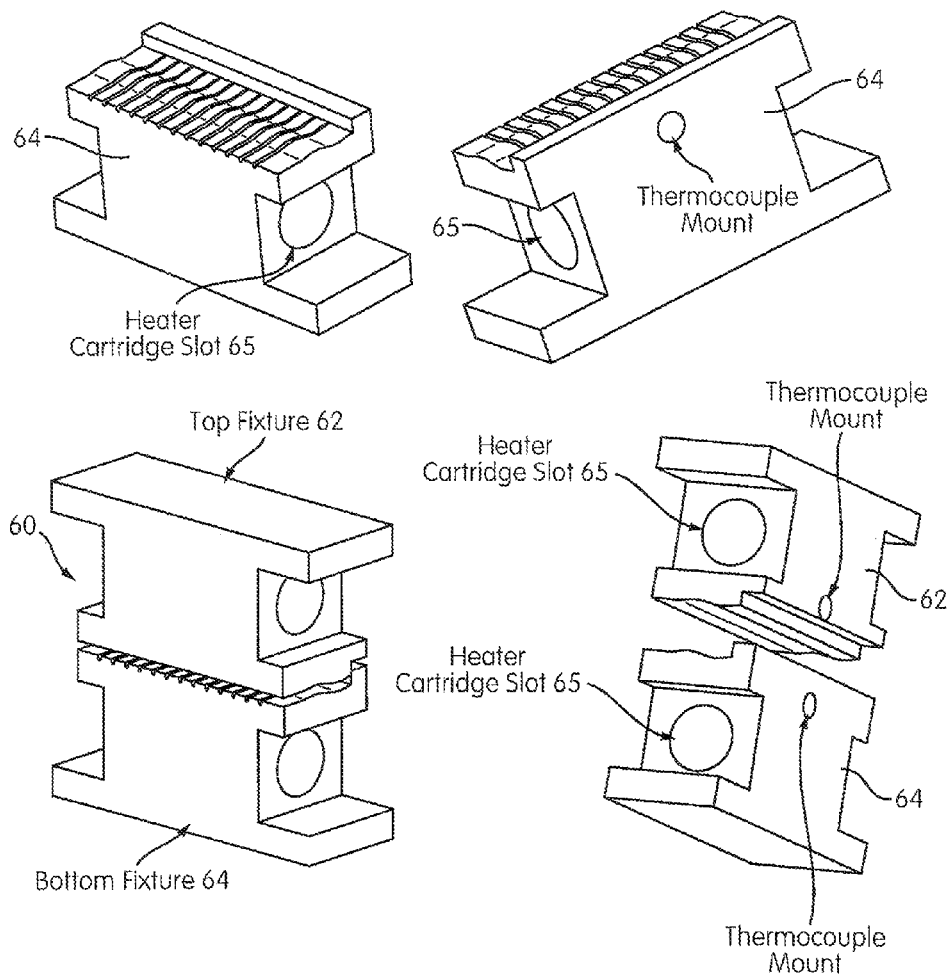
FIG. 11 is perspective views of a third embodiment of the present invention.
Figure 12:
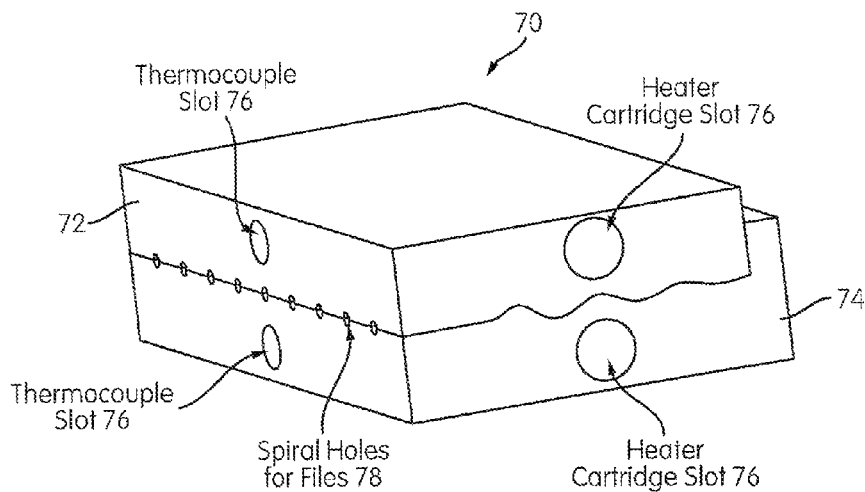
FIG. 12 is a perspective view of a forth embodiment of the present invention.
Figure 13:
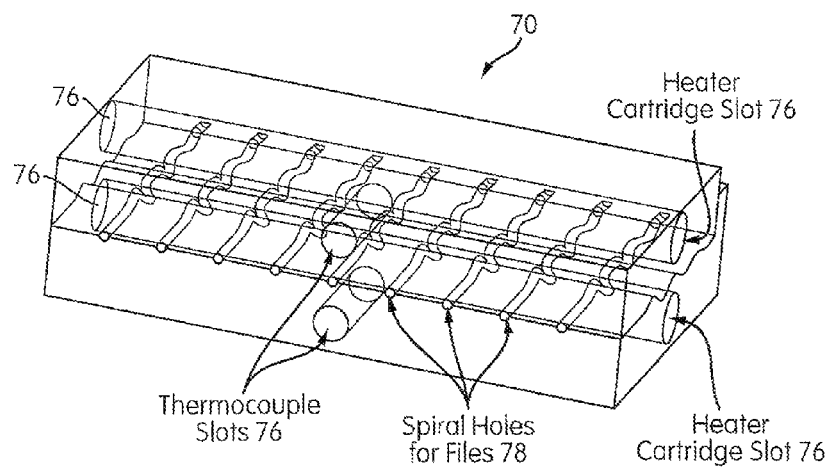
FIG. 13 is a transparent perspective view of the forth embodiment shown in FIG. 12.
Figure 14:
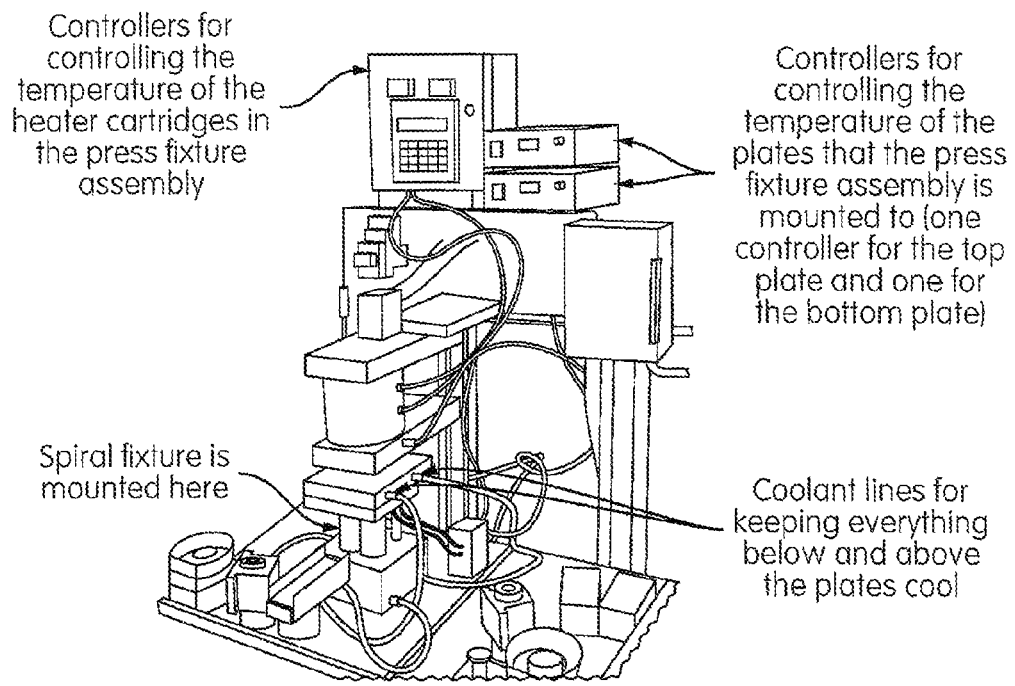
FIG. 14 is a perspective view of a fifth embodiment of the present invention.
Figure 15:
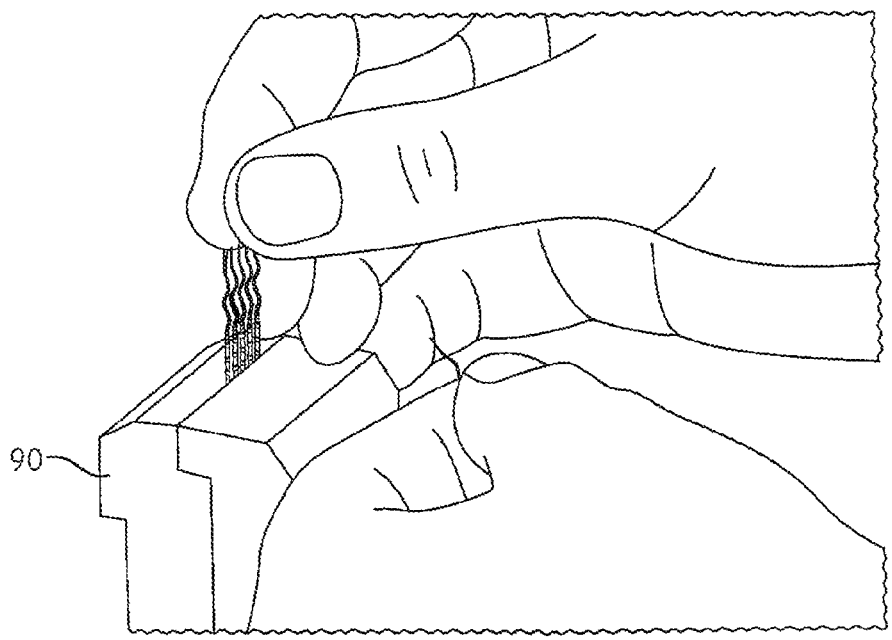
FIG. 15 is a perspective view of a sixth embodiment of the present invention.
Figure 16:
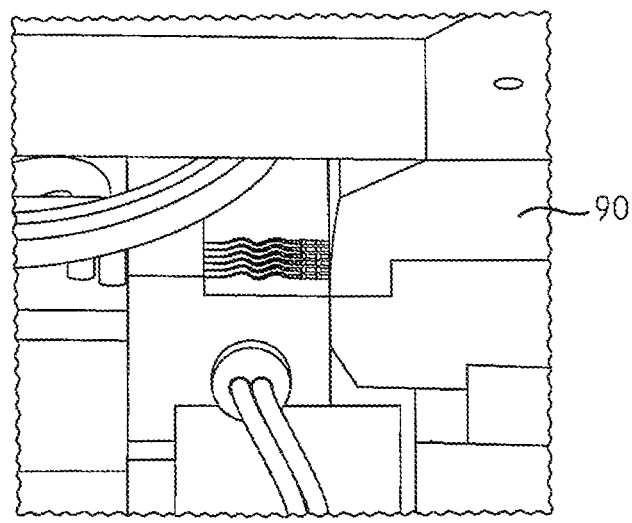
FIG. 16 is a perspective view of a seventh embodiment of the present invention.
Figure 17:
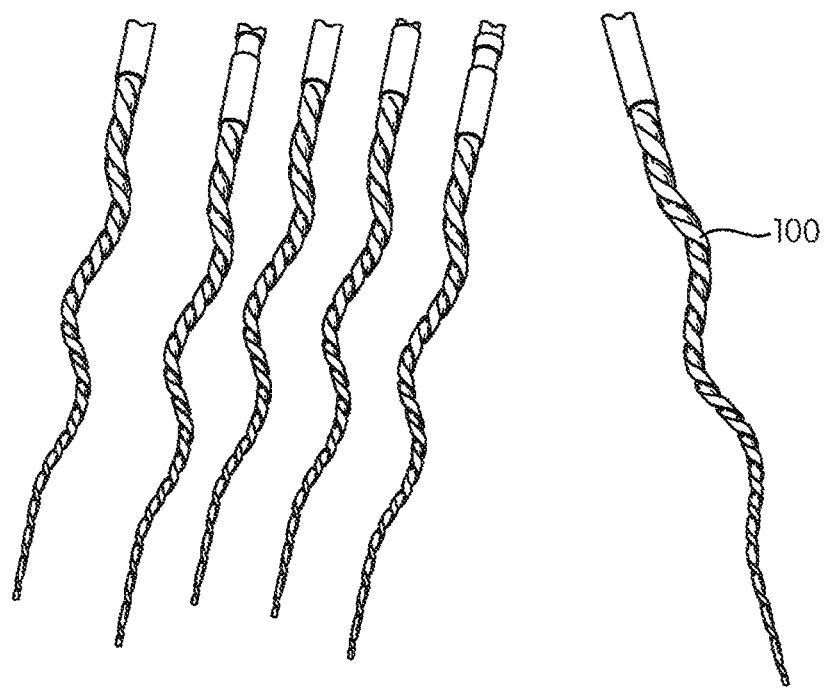
FIG. 17 is a perspective view of an eighth embodiment of the present invention.

Desirably, a typical shape set time and temperature may be approximately 450° C.-550° C. (e.g., about 500° C.) for about 7-15 minutes (e.g., 10 minutes), which allows the file to take on a different permanent shape. FIGS. 2, 3, and 4 show the 2D fixture 10 concept used to shape set the file in one plane (e.g., 2D nonlinear file). After the file is shape set into the 2 dimensional shape, the file is then placed into the 3D fixture 30 where the fixture is maintained at a desired temperature where it shape sets the file to the desired geometry (e.g., 3D nonlinear file). A typical shape set time and temperature may be approximately 450° C.-550° C. (e.g., about 500° C.) for about 7-15 minutes (e.g., 10 minutes) which allows the file to take on a different permanent shape (e.g., 3D nonlinear file). FIGS. 6, 7, 8, and 9 show the fixture concept used to shape set the file in 3 dimensions into a spiral shape. FIG. 11 shows a production version of the 2D fixture 60 for shape setting a plurality of 2D non-linear files. Fixture 60 may include a top mating portion 62 and a bottom mounting portion 64, where a heater cartridges (not shown) would be placed into the fixture heat slots 65 to heat and maintain the fixture to a desired temperature while the files are being shape set in one plane. The thermocouple slot 65 in the fixture is used to monitor the fixture temperature and signal the controller when heat is needed to be delivered to the fixture to keep the temperature constant. FIGS. 12 and 13 show a another 3D fixture 70 for shape-setting a plurality of 3D non-linear files. Fixture 70 may include a top mating portion 72 and a bottom mating portion 74 and spiral grooves 78 for receiving a 2D shape-set nonlinear file. It is appreciated that heater cartridges (not shown) would be placed into the fixture 70 through slots 76 to heat and maintain the fixture to a desired temperature while the files are being shape set 3 dimensionally into a spiral configuration. The thermocouple slot 76 in the fixture 70 is used to monitor the fixture temperature and signal the controller when heat is needed to be delivered to the fixture to keep the temperature constant. FIG. 14 shows an example of a machine set-up for the process where there is a controller used to monitor and keep the temperature constant on either the 2D or 3D fixture and the top and bottom plates of the fixtures are contacting 2 heater plates that are also heated to prevent the fixtures from losing heat during the process. FIG. 15 shows an example of a clamp 90 used to hold the files in place. Once the files are loaded into the clamp, the clamp is aligned to either the 2D or 3D fixture and the files are fed into the fixture via the clamp 90 and held there for a desired time (see FIGS. 15 and 16). Once the time is complete, the operator removes the clamp from either the 2D or 3D fixture where the files are allowed to cool and be removed. FIG. 17 is an example of what the spiral file 100 looks like after it has been shape set.

It is appreciated that in heating the instrument using resistance heating, a pair of spaced apart electrode contacts, which form an electrically conducting junction to the instrument or a portion therebetween, are in electrical communication with a source of electrical power (e.g., a generator, batteries, or otherwise). Once the contacts are positioned about the instrument, electricity will flow between the spaced apart contacts, thereby providing the heat sufficient for carrying out the specific heat treatment. As discussed above, in some instances, if only certain portions of the instrument are to be subjected to a heat treatment cycle, the contacts may be disposed so as to deliver electrical current only to those portions of the instrument. Accordingly, all of such embodiments are within the scope of this invention. Also, in some instances, certain portions of an instrument may be subjected to specific heat treatment steps separate from the heat treatment steps applied to the remainder of the instrument. For example, an entire instrument may be heat treated so as to induce a first metallurgical transition therein (e.g., non-superelastic heat-treatment), and selected portions of that instrument then retreated to convert those selected portions to a specific geometry (e.g., nonlinear file heat-treatment) and/or a second metallurgical state. For example, an instrument may be so processed to produce a high hardness member having selected areas of low hardness therein.

It will be further appreciated that functions or structures of a plurality of components or steps may be combined into a single component or step, or the functions or structures of one-step or component may be split among plural steps or components. The present invention contemplates all of these combinations. Unless stated otherwise, dimensions and geometries of the various structures depicted herein are not intended to be restrictive of the invention, and other dimensions or geometries are possible. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention. The present invention also encompasses intermediate and end products resulting from the practice of the methods herein. The use of "comprising" or "including" also contemplates embodiments that "consist essentially of" or "consist of" the recited feature.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

The invention claimed is:

1. A method for manufacturing at least one nonlinear file comprising the steps of:

providing a file having a shaft and a file axis;

providing a first fixture having a first file groove for receiving the shaft, the first file groove being defined by one or more first displacement members;

providing a second fixture having a second file groove for receiving the shaft of the shape-set nonlinear file, the second file groove being defined by one or more second displacement members;

inserting at least one portion of the shaft into the first file groove, the at least one portion of the shaft including a first portion of the shaft;

contacting the first portion of the shaft with a first displacement member of the one or more first displacement members such that the first portion of the shaft is displaced from the file axis thereby forming a first offset portion of the shaft, the first offset portion of the shaft and the file axis defining a first file plane;

heating the first offset portion of the shaft while inserted in the first fixture to a temperature from 200° C. to less than the melting point of the file for a time period from 1 minute to 640 minutes to shape-set the first offset portion of the shaft thereby forming a shape-set non-linear file;

inserting the first portion, a second portion, or both of the shaft of the shape-set nonlinear file into the second file groove;

contacting the first portion, the second portion, or both of the shaft with a first displacement member of the one or more second displacement members such that the first portion, the second portion, or both of the shaft is displaced from the first file plane thereby forming a second offset portion of the shaft, the second offset portion of the shaft and the file axis defines a second plane that is different from the first plane; and heating the second offset portion of the shaft while inserted in the second fixture to a temperature from 200° C. to less than the melting point of the file for a time period from 1 minute to 640 minutes to shape-set the second offset portion of the shaft thereby forming a shape-set three-dimensional nonlinear file.

2. The method of claim 1, wherein the shape-set nonlinear file is removed from the first fixture prior to being inserted into the second fixture.

3. The method of claim 1, wherein the file is formed of a material selected from the group consisting of nickel, titanium, and mixtures thereof.

4. The method of claim 1, wherein the shape-set nonlinear file is a shape-set nonlinear superelastic file.

5. The method of claim 1, wherein the first offset portion of the shaft along the first file plane is orientated along the second groove plane of the second file groove, wherein the shape of the first offset portion of the shaft along the first file plane generally corresponds to the shape of the second file groove along the second groove plane.

6. The method of claim 1, wherein the heating step of the first offset portion of the shaft, the portion of the shaft is heated to a temperature from 300° C. to 650° C. for a time period from 1 minute to 45 minute to shape-set the portion of the shaft thereby forming the shape-set nonlinear file.

7. The method of claim 1, wherein the heating step of the first offset portion of the shaft, the portion of the shaft is heated to a temperature from 350° C. to 600° C. for a time period from 3 minutes to 30 minutes to shape-set the portion of the shaft thereby forming the shape-set nonlinear file.

8. The method of claim 1, wherein the heating step of the first offset portion of the shaft, the portion of the shaft is heated to a temperature from 450° C. to 550° C. for a time period from 5 minutes to 20 minutes to shape-set the portion of the shaft thereby forming the shape-set nonlinear file.

9. The method of claim 1, wherein the heating step of the second offset portion of the shaft, the portion of the shaft is heated to a temperature from 300° C. to 650° C. for a time period from 1 minute to 45 minute to shape-set the portion of the shaft thereby forming the shape-set nonlinear file.

10. The method of claim 1, wherein the heating step of the second offset portion of the shaft, the portion of the shaft is heated to a temperature from 350° C. to 600° C. for a time period from 3 minutes to 30 minutes to shape-set the portion of the shaft thereby forming the shape-set nonlinear file.

11. The method of claim 1, wherein the heating step of the second offset portion of the shaft, the portion of the shaft is heated to a temperature from 450° C. to 550° C. for a time period from 5 minutes to 20 minutes to shape-set the portion of the shaft thereby forming the shape-set nonlinear file.

12. The method of claim 1, further comprising the step of contacting a second portion of the shaft with a second displacement member of the one or more displacement members such that the second portion of the shaft is displaced from the file axis thereby forming a second offset portion of the shaft, wherein the first offset portion of the shaft and the file axis define a first plane and the second offset portion defines a second plane different from the first plane.

13. The method of claim 1, further comprising the step of contacting a second portion of the shaft with a second displacement member of the one or more displacement members such that the second portion of the shaft is displaced from the file axis thereby forming a second offset portion of the shaft, wherein the first offset portion of the shaft and the file axis define a first plane and the second offset portion defines a second plane different from the first plane.

14. A method for manufacturing at least one nonlinear file comprising the steps of:

providing a linear file having a shaft and a file axis;

providing a first fixture having a first mating portion and a second mating portion, each mating portion including a surface, at least one of the surfaces of the first and second mating portions having a first file groove for receiving the shaft, the first file groove extending along a first groove plane that is defined by a first groove axis and one or more first displacement members;

inserting a first portion of the shaft into the first file groove so that the file axis along the first portion of the shaft and the first groove axis along the first file groove are generally coaxial;

moving at least one of surfaces towards one another so that a first displacement member of the one or more first displacement members displaces the first portion of the shaft from the file axis along the first groove plane thereby forming a first offset portion of the shaft, the first offset portion of the shaft and the file axis defining a first file plane;

heating the first offset portion of the shaft while inserted in the first fixture to a temperature from 200° C. to less than the melting point of the file for a time period greater than 5 minutes but less than 640 minutes to shape-set the first offset portion of the shaft thereby forming a shape-set nonlinear file;

removing the shape-set nonlinear file from the first fixture;

providing a second fixture having a first mating portion and a second mating portion, each mating portion including a surface, at least one of the surfaces of the first and second mating portions having a second file groove for receiving a nonlinear shaft of the shape-set nonlinear file, the second file groove having a second groove axis, one or more second displacement members, and a second groove opening that extends along the at least one of the surfaces of the first and second mating portions, the second groove opening generally corresponding to the shape of the first offset portion along the first file plane;

inserting a first portion of the nonlinear shaft into the second groove opening;

moving at least one of surfaces towards one another so that a first displacement member of the one or more second displacement members displaces the first portion of the nonlinear shaft away from the first file plane thereby forming a second offset portion of the nonlinear file; and heating the second offset portion of the shaft while inserted in the second fixture to a temperature from 200° C. to less than the melting point of the file for a time period greater than 5 minutes but less than 640 minutes to shape-set the second offset portion of the nonlinear file thereby forming a shape-set three-dimensional nonlinear file.

15. The method of claim 14, wherein the nonlinear 3D file is formed of a material selected from the group consisting of nickel, titanium, and mixtures thereof.

16. The method of claim 14, wherein the shape-set nonlinear file is a shape-set nonlinear superelastic file.

17. The method of claim 14 wherein the first offset portion of the shaft along the first file plane is orientated along the second groove plane of the second file groove, wherein the shape of the first offset portion of the shaft along the first file plane generally corresponds to the shape of the second file groove along the second groove plane.

18. The method of claim 14, wherein the heating step, the first offset portion, the second offset portion, or both is heated to a temperature from 300° C. to 650° C. for a time period from 5 minutes to 45 minute to shape-set the portion of the shaft thereby forming the shape-set nonlinear file.

19. The method of claim 14, wherein the heating step, the first offset portion, the second offset portion, or both is heated to a temperature from 350° C. to 600° C. for a time period from 7 minutes to 30 minutes to shape-set the portion of the shaft thereby forming the shape-set nonlinear file.

20. The method of claim 14, wherein the heating step, the first offset portion, the second offset portion, or both is heated to a temperature from 450° C. to 550° C. for a time period from 8 minutes to 20 minutes to shape-set the portion of the shaft thereby forming the shape-set nonlinear file.

21. The method of claim 14, further comprising the step of contacting a second portion of the shaft with a second displacement member of the one or more first displacement members such that the second portion of the shaft is displaced from the file axis thereby forming a third offset portion of the shaft, wherein the first offset portion and third offset portion of the shaft and the file axis define a first plane and the second offset portion defines a second plane different from the first plane.

22. A method for manufacturing at plurality of nonlinear files comprising the steps of:
providing a plurality of files having a shaft and a file axis;
providing a first fixture having a first mating portion and a second mating portion, each mating portion including a surface with a plurality of first file grooves having a first groove opening for receiving at least a portion of the shafts of the plurality of files, the first file grooves of the first mating portion surface corresponding to the opposing first file groove of the second mating portion, wherein the groove openings include a base surface having one or more first displacement members;
inserting a first portion of the shafts into the first file grooves along the groove openings, wherein the groove openings generally correspond to the shape of the first portion of the shafts along the file axes;
moving at least one of surfaces towards one another so that a first displacement member of the one or more first displacement members displaces the first portion of the shafts from the file axes thereby forming a plurality first offset portions of the shafts, each first offset portion of each shaft and each file axis define a first file plane;
heating the first offset portions of the shafts while inserted in the first fixture to a temperature from 200° C. to less than the melting point of the file for a time period from 5 minutes to 640 minutes to shape-set the first offset portions of the shafts thereby forming a plurality of shape-set nonlinear files;
removing the shape-set nonlinear files from the first fixture;
providing a second fixture having a first mating portion and a second mating portion, each including a surface, the surfaces of the first and second mating portions having a plurality of second file grooves with second groove openings extending along the respective surface, the second file grooves of the first mating portion surface corresponding to the opposing first file grooves of the second mating portion, wherein the second groove openings include a base surface having one or more second displacement members;
inserting a first portion of a nonlinear shafts of the nonlinear files into the second groove openings;
moving at least one of surfaces towards one another so that a first displacement member of the one or more second displacement members of each of the second file grooves displaces the first portion of the nonlinear shafts away from the first file planes thereby forming a second offset portion of the nonlinear files; and
heating the second offset portion of the nonlinear shafts while inserted in the second fixture to a temperature from 200° C. to less than the melting point of the files for a time period from 5 minutes to 640 minutes to shape-set the second offset portion of the nonlinear shafts thereby forming a plurality of shape-set three-dimensional nonlinear files.

23. The method of claim 22, wherein the nonlinear 3D files are formed of a material selected from the group consisting of nickel, titanium, and mixtures thereof.

24. The method of claim 22, wherein the shape-set nonlinear files are a plurality of shape-set nonlinear superelastic file.

25. The method of claim 22 wherein the first offset portions of the shafts along the first file planes are orientated along the second groove planes of the second file grooves, wherein the shape of the first offset portions of the shafts along the first file planes generally correspond to the shape of the second file grooves along the second groove planes.

26. The method of claim 22, wherein the heating step, the first offset portions, the second offset portions, or both are heated to a temperature from 300° C. to 650° C. for a time period from 5 minutes to 45 minute to shape-set the portions of the shafts thereby forming the shape-set nonlinear files.

27. The method of claim 22, wherein the heating step, the first offset portions, the second offset portions, or both are heated to a temperature from 350° C. to 600° C. for a time period from 7 minutes to 30 minutes to shape-set the portions of the shafts thereby forming the shape-set nonlinear files.

28. The method of claim 22, wherein the heating step, the first offset portions, the second offset portions, or both is heated to a temperature from 450° C. to 550° C. for a time period from 8 minutes to 20 minutes to shape-set the portions of the shafts thereby forming the shape-set nonlinear files.

29. The method of claim 22, further comprising the step of contacting a second portion of the shafts with a second displacement member of the one or more first displacement members of each first file groove such that the second portions of the shafts are displaced from the file axes thereby forming a third offset portion of the shafts, wherein the first offset portions and third offset portions of the shafts and the file axes define a plurality of first planes and the second offset portions defines a plurality of second planes different from the first planes.

\* \* \* \* \*